United States Patent [19]

Randall

[11] Patent Number: 4,572,323

[45] Date of Patent: Feb. 25, 1986

[54] HEARING PROTECTORS

[75] Inventor: Mervyn D. G. Randall, Surrey, England

[73] Assignee: Racal Safety Limited, Wembley, England

[21] Appl. No.: 591,455

[22] Filed: Mar. 20, 1984

[30] Foreign Application Priority Data

Mar. 28, 1983 [GB] United Kingdom ............... 8308484

[51] Int. Cl.⁴ .............................................. H04R 25/00
[52] U.S. Cl. ................................ 181/129; 179/156 R; 179/182 R; 2/209
[58] Field of Search ............ 181/129; 179/184, 156 R, 179/179, 182 R; 2/209

[56] References Cited

U.S. PATENT DOCUMENTS

| | | | |
|---|---|---|---|
| 3,051,961 | 9/1962 | Clark | 181/129 X |
| 3,908,200 | 9/1975 | Lundin | 2/209 |
| 4,057,856 | 11/1977 | Aho | 2/209 |

Primary Examiner—L. T. Hix
Assistant Examiner—Brian W. Brown
Attorney, Agent, or Firm—Scrivener Clarke Scrivener and Johnson

[57] ABSTRACT

A hearing protecting device comprises a shell defining a hollow enclosure, which may be provided with sound absorbing material, with an open mouth, which is, in use, placed over the ear. A resiliently deformable seal of sound absorbing material is provided along the periphery of the open mouth to seal against the shell and the wearer, and is releasably retained in place by releasable retaining means which cooperate with an inner portion of the sealing means and with an inner edge portion of the mouth of the enclosure. The retaining means may comprise an annular member made integral with the sealing means and which extends round the inner edge of the mouth to overlie and engage an inner surface of the shell, or a member separate from the sealing means which retains an inner portion of the sealing means relative to the inner edge of the mouth of the shell.

7 Claims, 6 Drawing Figures

HEARING PROTECTORS

The present invention relates to improvements in hearing protectors which generally comprise two shells to be placed one over each ear and which are generally supported on a band which extends around the head of the wearer and biases the shells against the wearer's ears.

The shells are intended to protect the inner ear against external sound waves and are therefore intended to absorb at least a substantial amount of the energy of external waves so as to prevent it being transmitted to the inner ear. To prevent such sound waves reaching the inner ear through gaps between the shell and the wearer's head or ear, the shells are normally provided with peripheral resiliently deformable seals which seal against the shell and the wearer's head or ear.

According to the present invention there is provided a hearing protecting device comprising a shell defining a hollow enclosure with an open mouth which is, in use, placed over the ear, a resiliently deformable annular seal extending along the open mouth of the enclosure for sealing against the shell and against the wearer, and retaining means for releasably retaining the sealing means relative to the shell, which retaining means cooperate with an inner portion of the sealing means and an inner portion of the mouth of the enclosure.

The retaining means may include a member of relatively inflexible material which is made integral with the sealing means along an inner edge portion thereof, and which extends round an inner edge portion of the mouth of the enclosure and along an inner surface of the shell.

Advantageously, the mouth of the enclosure has an annular surface on which the sealing means is located and which is provided by a surface of an inwardly extending flange on the shell, the retaining means comprising a flange which extends over the inner surface of the flange on the shell.

The retaining means may alternatively comprise a member, for example in the form of a clip, which is separate from the sealing means and which releasably engages an inner edge portion of the sealing means and an inner edge portion of the mouth of the shell to retain the sealing means relative to the shell.

The hearing protecting device may be dimensioned to fit over or around the ear and may include or form an earphone.

Two hearing protecting devices as described above may be mounted on a band which, in use, extends around the head of the wearer and biases the devices against the wearer's head, to provide a hearing protecting assembly.

Embodiments according to the present invention will now be described, by way of example only, with reference to the accompanying drawings, in which.

Figure 1:
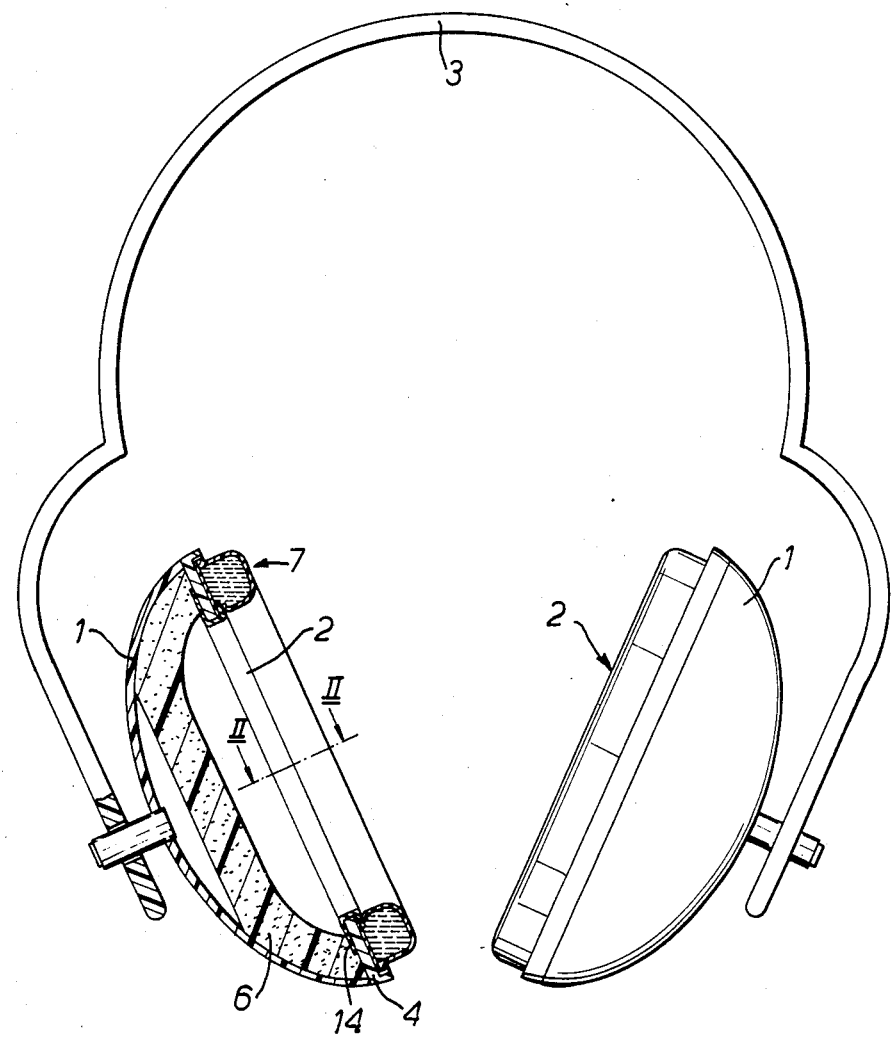
FIG. 1 is a part sectional part elevational view of an embodiment of hearing protecting assembly comprising an embodiment of a hearing protecting device according to the present invention.

The hearing protecting assembly shown in FIG. 1 comprises a pair of shells 1, each defining a hollow enclosure with an open mouth 2, which, in use, are located over the ears of the wearer. The shells 1 are mounted in any suitable conventional manner on a band 3 of any suitable conventional shape which extends around the head of the wearer and biases the shells 1 against the wearer's head. Advantageously either the shells 1 are adjustably mounted on the band 3 or the band 3 is adjustable in length, to accommodate variations in dimensions of heads.

The shells 1 are preferably moulded of plastics material and include flanges 4, which may be formed separately and then fixed to the shells 1, extending around the open mouth of the enclosure of the shell and providing a planar surface 5. Suitable sound absorbing material 6 is provided within each shell and an annular seal 7 is located on surface 5 for sealing the gap between shell 1 and the wearer's head.

Figure 2:
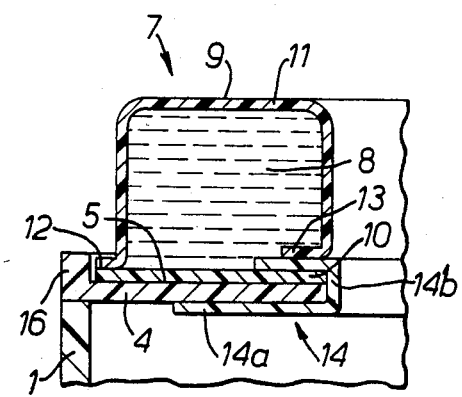
FIG. 2 is an enlarged section on the line II—II of FIG. 1.
Figure 3:
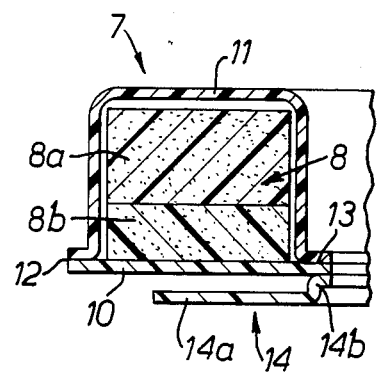
FIGS. 3 to 6 show modifications of the sealing means of FIGS. 1 and 2.

As shown more clearly in FIG. 2, the seal 7 comprises a resiliently deformable sound absorbing material 8, which may for example comprise a fluid, as shown in FIG. 2, or layers 8a, 8b of suitable sound absorbing resiliently compressible foam, as shown in FIG. 3, which is enclosed in a protective casing 9. The casing 9 comprises a base member 10 of relatively rigid material which overlies flange 4 and a cover member 11 of relatively flexible material which can be formed to a suitable shape and surrounds the remainder of the seal. Members 10 and 11 may for example be heat sealed or welded together at 12 and 13 along their outer and inner edges. The seal 7 is retained in place on flange 4 by an annular member 14 of relatively inflexible material, for example p.v.c. sheet material, which is made integral with the seal. The member 14 extends from the inner edge of the seal around the inner edge of flange 4 to engage the inner surface of flange 4. As shown in FIG. 2, member 14 is shaped to provide a flange portion 14a which extends under flange 4 and a portion 14b which is welded at 13 to an inner portion of the seal 7. The material of member 14 has sufficient flexibility that it can be deformed to locate the seal on the flange 4 with the flange 14a beneath flange 4, but will yet not permit easy removal of the seal 7.

Figure 4:
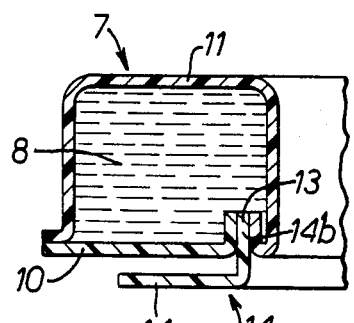
Figure 5:
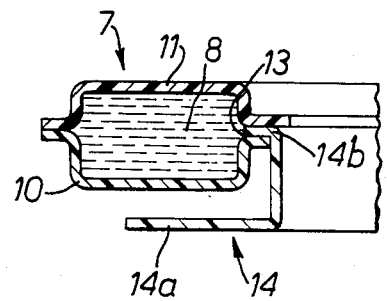

It will be appreciated that the fixing of member 14 to the seal 7 can be achieved in a number of different ways subsequent to manufacture of the seal 7 or as part of the manufacture of the seal, and examples of the latter are shown in FIGS. 3, 4 and 5, in which the same reference numerals have been used for like parts.

By closely shaping flange 14a of member 14 to the flange 4, it is found that this arrangement provides an excellent acoustic seal between the seal 7 and the shell 1, not only because there is close contact between the respective parts but also because it provides a tortuous path for any sound waves penetrating between casing part 10 and flange 4.

In all the above described arrangements, the seal 7 is retained relative to the shell by the member 14 which is made integral with an inner edge portion of the seal 7 and cooperates with the inner edge of the flange 4.

Figure 6:
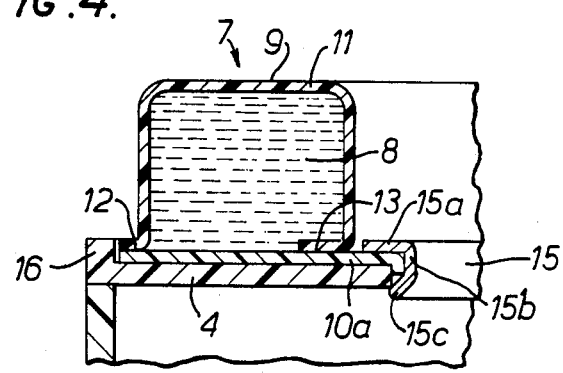

Alternatively, the seal 7 can be retained relative to the shell by a retaining member separate from the seal which cooperates with an inner portion of the seal 7 and the flange 4. For example as shown in FIG. 6, the retaining member may take the form of an annular clip 15 having a generally inverted L-shaped cross-section, the base portion 15a of which overlies the outer surface of flange 4, the upright portion 15b engaging within flange 4 with a friction fit. The end portion 15c of the upright portion 15b may be formed with an enlarged diameter so that it positively engages beneath the flange 4 to positively hold the clip 15 in place. The inner edge of the seal is provided with a flange portion 10a, as shown an extension of member 10, which is trapped between the base 15a of the clip and the flange 4. The flange portion 10a of the seal may be dimensioned as shown so that it is forced by the clip 15 over the edge of flange 4 to more positively retain the seal in place and increase the sealing effect. The clip 15 is made of a resilient material, for example metal or plastics, to be resiliently and removably engageable with the flange 4. Its flexibility may be increased by providing the clip with a split so that it has the form of a split ring.

For aesthetic reasons, the flange 4 may as shown in FIG. 2 be provided with an upstanding rim 16 which extends over and visually covers the edges of casing parts 10 and 11 at join 12.

In a preferred embodiment, the casing 9 of the seal is made of a flexible p.v.c., with the material of casing part 10 being less flexible than that of casing part 11. Where the seal 7 is filled with a liquid, the liquid may comprise a mixture of glycerine and distilled water. Where the seal 7 is provided with layers of resiliently compressible foam plastics, one, two or more layers of foam plastics having different characteristics may be provided. Where the seal is filled with foam plastics material, the casing part 11 may be apertured to vent air within the casing.

What is claimed is:

1. A hearing protecting device for protecting the hearing of a wearer comprising a shell defining a hollow enclosure with an open mouth which is, in use, placed over an ear of the wearer, a resiliently deformable annular sealing means extending along said open mouth of said enclosure for sealing against said shell and against the wearer, said sealing means having an inner peripheral portion, said shell comprising an annular flange at said open mouth, said flange having inner and outer surfaces and extending inwardly from the periphery of the mouth across the mouth of the enclosure and providing an annular surface which said sealing means overlies and against which said sealing means seals, said flange having an inner peripheral edge portion, and retaining means for releasably retaining said sealing means relative to said shell comprising an annular member made integral with said inner peripheral portion of said sealing means and adapted to extend around the inner peripheral edge portion of the flange and underlie the inner surface of said flange, said annular member and said inner surface comprising the sole retaining means for said sealing means.

2. A hearing protecting device as claimed in claim 1, wherein said retaining means comprises an outwardly extending flange for underlying said flange on said shell.

3. A hearing protecting assembly comprising two hearing protecting devices as claimed in claim 1, said devices being mounted on a band which, in use, extends around the head of the wearer and biases said devices against the wearer's head.

4. A hearing protecting device for protecting the hearing of a wearer comprising: a shell defining a hollow enclosure with an open mouth which is in use placed over an ear of the wearer; an annular flange at said open mouth, said flange having inner and outer surfaces and extending inwardly from the periphery of the mouth across the mouth of the enclosure, resiliently deformable annular sealing means extending along said outer surface of said flange for sealing against said outer surface and against the wearer, said sealing means comprising sound absorbing material enclosed in a protective annular casing, said casing comprising an annular base member which overlies and engages said outer surface of said flange and a flexible annular cover member, said members being fixed together along inner and outer peripheries thereof; and retaining means for releasably retaining said sealing means relative to said shell, said retaining means comprising an annular member fixed to said sealing means along the fixing of said inner peripheries of said casing members and extending therefrom to underly and engage said inner surface of said flange, said annular member and said inner surface of said flange comprising the sole retaining means for said sealing means.

5. A hearing protecting device as claimed in claim 4, wherein said annular member is of relatively inflexible material.

6. A hearing protecting device comprising: a shell defining a hollow enclosure with an open mouth which is in use placed over the a wearer's ear; a resiliently deformable annular seal extending along a surface of said shell at said open mouth of said enclosure for sealing against said shell surface and against the wearer, said seal comprising sound absorbing material enclosed in a protective annular casing, said casing comprising an annular base member which overlies said surface of said shell and a flexible annular cover member, said members being fixed together along inner and outer peripheries thereof; and retaining means for releasably retaining said sealing means relative to said shell, said retaining means comprising a member separate from said sealing means and said shell and which engages a portion of said sealing means and retains it relative to an inner edge portion of said mouth of said shell, said portion of said sealing means comprising a flange extending freely from the fixing of said inner peripheries of said casing members of said sealing means.

7. A hearing protecting device protecting the hearing of a wearer comprising a shell defining a hollow enclosure with an open mouth which, in use, is placed over an ear of the wearer, a resiliently deformable annular sealing means extending along said open mouth of said enclosure for sealing against said shell and against the wearer, said shell comprising an annular flange at the open mouth thereof, said flange extending inwardly from the periphery of the mouth across the mouth of the enclosure and providing an annular surface on which said sealing means is located and against which said sealing means seals, and retaining means separate from said sealing means and said shell for releasably retaining said sealing means relative to said shell solely by the inner periphery thereof and comprising an annular member which releasably engages over an inner peripheral portion of said sealing means and under the inner periphery of said flange to hold said sealing means relative to said flange.

* * * * *